US007737282B2

(12) United States Patent
Fujishima et al.

(10) Patent No.: US 7,737,282 B2
(45) Date of Patent: Jun. 15, 2010

(54) BENZIMIDAZOLE COMPOUND CRYSTAL

(75) Inventors: Akira Fujishima, Hyogo (JP); Isao Aoki, Hyogo (JP); Keiji Kamiyama, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/393,409

(22) Filed: Feb. 26, 2009

(65) Prior Publication Data

US 2009/0163553 A1 Jun. 25, 2009

Related U.S. Application Data

(63) Continuation of application No. 12/006,845, filed on Jan. 7, 2008, now Pat. No. 7,569,697, which is a continuation of application No. 11/149,903, filed on Jun. 10, 2005, now Pat. No. 7,339,064, which is a continuation of application No. 10/655,114, filed on Sep. 4, 2003, now Pat. No. 6,939,971, which is a continuation of application No. 10/243,329, filed on Sep. 13, 2002, now Pat. No. 6,664,276, which is a continuation of application No. 09/674,624, filed as application No. PCT/JP00/03881 on Jun. 15, 2000, now Pat. No. 6,462,058.

(30) Foreign Application Priority Data

Jun. 17, 1999 (JP) ................................. 11-171509

(51) Int. Cl.
C07D 215/38 (2006.01)
(52) U.S. Cl. .................................. 546/273.4; 546/273.7
(58) Field of Classification Search .............. 546/273.4, 546/273.7
See application file for complete search history.

(56) References Cited

U.S. PATENT DOCUMENTS

| | | | |
|---|---|---|---|
| 4,628,098 A | 12/1986 | Nohara et al. | |
| 5,840,737 A | 11/1998 | Phillips | |
| 6,462,058 B1 | 10/2002 | Fujishima et al. | |
| 6,664,276 B2 | 12/2003 | Fujishima et al. | |
| 6,939,971 B2 | 9/2005 | Fujishima et al. | |
| 7,339,064 B2 | 3/2008 | Fujishima et al. | |

FOREIGN PATENT DOCUMENTS

| | | |
|---|---|---|
| DE | 40 35 455 | 5/1992 |
| EP | 0 174 726 | 3/1986 |
| EP | 0 302 720 | 2/1989 |
| WO | 92/08716 | 5/1992 |
| WO | 96/02535 | 2/1996 |
| WO | 96/17077 | 6/1996 |
| WO | 97/02261 | 1/1997 |
| WO | 98/21201 | 5/1998 |
| WO | 98/22118 | 5/1998 |
| WO | 98/28294 | 7/1998 |
| WO | 99/38512 | 8/1999 |
| WO | 99/38513 | 8/1999 |
| WO | 99/56698 | 11/1999 |

OTHER PUBLICATIONS

Robinson, Malcolm, Annals of Internal Medicine, vol. 124, vol. 10, pp. 859-867, 1996.*
U.S. Pharmacopia, #23, National Formulary #18 (1995), pp. 1843-1844.
Concise Encyclopedia Chemistry, Translated and revised by Mary Eagleson (1994), Walter de Gruyter: New York, pp. 872-873.
Rouhi, A. Maureen, "the Rigt Stuff", Journal C&E News (Feb. 24, 2003), pp. 32-35.
Katsuki, H. et al., "Determination of R(+)- and S(−)- Lansoprazole using Chiral Stationary-Phase Liquid Chromatography and Their Enantioselective Pharmacokinetics in Humans", Pharmaceutical Research, (1996), vol. 13, No. 4, pp. 611-615.
Curin, A. et al., "Study of Crystal Modifications of Lansoprazole using FT-IR Spectroscopy, Soild-State NMR Spectroscopy and FT-Raman Spectroscopy", Farm vestn (1997), vol. 48, pp. 290-291.
Vrecer, F. et al., "Study of Influence of Temperature and Grinding on the CrystallineState of Lansoprazole", Farm vestn, (1997), vol. 48, pp. 242-243.
Nagaya, H. et al., "Effects of the Enantiomers of Lansoprazole (AG-1979) on (H+ + K +)−ATPase Activity in Canine Gastric Microsomes and Acid Formation in Isolated Canine Parietal Cells", Biochemical Pharmacology, (1991), vol. 42, No. 10, pp. 1875-1878.
Hirschowitz, B. et al., "Long-Term Treatment with Lansoprazole for Patients with Zollinger-Ellison Syndrome", Aliment Pharmacol Ther (1996), vol. 10, pp. 507-522.
Figura, et al., "In-vitro activity of lansoprazole against Helicobacter pylori", Journal of Antimicrobial Chemotherapy, vol. 39, 1997, pp. 585-590.
Langtry, et al., "Lansoprazole", Drugs, vol. 54, No. 3, 1997, pp. 473-500.
Castell, et al., "Efficacy and Safety of lansoprazole in the treatment of erosive reflux esophagitis", The American Journal of Gastroenterology, vol. 91, No. 9, 1996, pp. 1749-1757.
Zimmermann, et al., "Lansoprazole: a comprehensive review", Pharmacotherapy, vol. 17, No. 2, 1997, pp. 308-326.
Katsuya, et al., "Lansoprazole reduces preoperative gastric fluid acidity and volume in children", Can J Anaesth., 1995, vol. 42, No. 6, pp. 467-472.
Borner, et al., "Separation of Lansoprazole Enantiomers in Human Serum by HPLC", Chromatographia, vol. 47, No. 3/4, Feb. 1998, pp. 171-175.
Arimori, et al., "Pharmacokinetic Differences Between Lansoprazole Enantiomers in Rats", J. Pharm. Pharmacol., 1998, vol. 50, pp. 1241-1245.
Landes, et al., "Clinical Pharmacokinetics of Lansoprazole", Clin. Pharmacokinet., 1995, vol. 28, No. 6, pp. 458-470.

(Continued)

Primary Examiner—D. Margaret Seaman
(74) Attorney, Agent, or Firm—Hamre, Schumann, Mueller & Larson, P.C.

(57) ABSTRACT

A novel crystal of (R)-2-[[[3-methyl-4-(2,2,2-trifluoroethoxy)-2-pyridinyl]methyl]sulfinyl]-1H-benzimidazole or a salt thereof of the present invention is useful for an excellent antiulcer agent.

4 Claims, No Drawings

OTHER PUBLICATIONS

"Experimental Organic Chemistry-Principle and Practice", Blackwell Scientific Publication 1989, pp. 127-132.

"Vogel's Textbook of Practical Organic Chemistry", Longman Scientific & Technical; Fifth Edition: 1989, pp. 141-142.

Byrn, "Solid State Chemistry of Drugs", Academic Press, 1982, pp. 10-13.

Opponent's Statement of Case filed in the matter of: Patent Application No. IL 145,996; *Teva Pharmaceutical Industries Ltd.* vs. *Takeda Pharmaceutical Company Limited*, Notice of Opposition filed Oct. 6, 2008, Opponent's Statement of Case filed Feb. 6, 2009—14 pages.

\* cited by examiner

BENZIMIDAZOLE COMPOUND CRYSTAL

This application is a continuation of application of Ser. No. 12/006,845, filed Jan. 7, 2008, which is a continuation of Ser. No. 11/149,903, filed Jun. 10, 2005, which is a continuation of Ser. No. 10/655,114, filed Sep. 4, 2003, which is a continuation of application Ser. No. 10/243,329, filed Sep. 13, 2002, which is a continuation of application Ser. No. 09/674,624, filed Nov. 3, 2000, which application is incorporated herein by reference.

TECHNICAL FIELD

The present invention relates to a crystal of a benzimidazole compound showing antiulcer action.

BACKGROUND ART

2-[[[3-methyl-4-(2,2,2-trifluoroethoxy)-2-pyridinyl]methyl]sulfinyl]-1H-benzimidazole or a salt thereof having an antiulcer action is reported in JP-A-61-50978, etc.

There is a demand for a more stable and excellently absorbable antiulcer agent.

DISCLOSURE OF INVENTION

Having chiral sulfur in the molecular structure thereof, 2-[[[3-methyl-4-(2,2,2-trifluoroetoxy)-2-pyridinyl]methyl]sulfinyl]-1H-benzimidazole occurs in two kinds of optical isomers. After extensive exploration, the present inventors succeeded in optically resolving and present inventors succeeded in optically resolving and crystallizing in the (R)-isomer of 2-[[[3-methyl-4-(2,2,2-trifluoroethoxy)-2-pyridinyl]methyl]sulfinyl]-1H-benzimidazole, for the first time found that this crystal serves satisfactorily as a pharmaceutical, made further investigation based on this finding, and developed the present invention.

Accordingly, the present invention relates to:

[1] a crystal of (R)-2-[[[3-methyl-4-(2,2,2-trifluoroethoxy)-2-pyridinyl]methyl]sulfinyl]-1H-benzimidazole or a salt thereof;

[2] a crystal of (R)-2-[[[3-methyl-4-(2,2,2-trifluoroethoxy)-2-pyridinyl]methyl]sulfinyl]-1H-benzimidazole;

[3] a crystal according to the above [2] wherein the X-ray powder diffraction analysis pattern has characteristic peaks at interplanar spacings (d) of 11.68, 6.77, 5.84, 5.73, 4.43, 4.09, 3.94, 3.89, 3.69, 3.41 and 3.11 Angstrom;

[4] a pharmaceutical composition which comprises the crystal according to the above [1];

[5] a pharmaceutical composition according to the above [4], which is for treating or preventing digestive ulcer;

[6] a method for treating or preventing digestive ulcer in a mammal in need thereof which comprises administering to said mammal an effective amount of the crystal according to the above [1] with a pharmaceutically acceptable excipient, carrier or diluent;

[7] use of the crystal according to the above [1] for manufacturing a pharmaceutical composition for treating or preventing digestive ulcer, and so forth.

The "salt" of "(R)-2-[[[3-methyl-4-(2,2,2-trifluoroethoxy)-2-pyridinyl]methyl]sulfinyl]-1H-benzimidazole or a salt thereof" includes, for example, metal salts, salts with organic bases, salts with basic amino acids, and so forth. Preferred are physiologically acceptable salts.

Metal salts include, for example, alkali metal salts such as sodium salt and potassium salt; and alkaline earth metal salts such as calcium salt, magnesium salt and barium salt. Salts with organic bases include, for example, salts with trimethylamine, triethylamine, pyridine, picoline, ethanolamine, diethanolamine, triethanolamine, dicyclohexylamine, N,N-dibenzylethylenediamine, etc. Salts with basic amino acids include, for example, salts with arginine, lysine, etc.

The crystal of (R)-2-[[[3-methyl-4-(2,2,2-trifluoroethoxy)-2-pyridinyl]methyl]sulfinyl]-1H-benzimidazole or a salt thereof may be a hydrate or not.

Said "hydrate" includes 0.5 hydrate to 5.0 hydrate. Among others, 0.5 hydrate, 1.0 hydrate, 1.5 hydrate, 2.0 hydrate and 2.5 hydrate are preferred. More preferred is 1.5 hydrate.

The crystal of (R)-2-[[[3-methyl-4-(2,2,2-trifluoroethoxy)-2-pyridinyl]methyl]sulfinyl]-1H-benzimidazole or a salt thereof can be produced by subjecting 2-[[[3-methyl-4-(2,2,2-trifluoroethoxy)-2-pyridinyl]methyl]sulfinyl]-1H-benzimidazole or a salt thereof to an optical resolution or subjecting 2-[[[3-methyl-4-(2,2,2-trifluoroethoxy)-2-pyridinyl]methyl]thio]-1H-benzimidazole to an asymmetrical oxidization to obtain the (R)-isomer, followed by crystallizing the resultant isomer.

Methods of optical resolution includes per se known methods, for example, a fractional recrystallization method, a chiral column method, a diastereomer method, and so forth. Asymmetric oxidation includes per se known method.

The "fractional recrystallization method" includes a method in which a salt is formed between a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.], which salt is separated by fractional recrystallization etc., and, if desired, subjected to a neutralization process, to give a free optical isomer.

The "chiral column method" includes a method in which a racemate or a salt thereof is applied to a column for optical isomer separation (chiral column). In the case of liquid chromatography, for example, optical isomers are separated by adding a racemate to a chiral column such as ENANTIO-OVM (produced by Tosoh Corporation) or the DAICEL CHIRAL series (produced by Daicel Corporation), and developing the racemate in water, a buffer (e.g., phosphate buffer), an organic solvent (e.g., hexane, ethanol, methanol, isopropanol, acetonitrile, trifluoroacetic acid, diethylamine, triethylamine, etc.), or a solvent mixture thereof. In the case of gas chromatography, for example, a chiral column such as CP-Chirasil-DeX CB (produced by GL Science) is used to separate optical isomers.

The "diastereomer method" includes a method in which a racemate and an optically active reagent are reacted (preferably, an optically active reagent is reacted to the 1-position of the benzimidazole group) to give a diastereomer mixture, which is then subjected to ordinary separation means (e.g., fractional recrystallization, chromatography, etc.) to obtain either diastereomer, which is subjected to a chemical reaction (e.g., acid hydrolysis, base hydrolysis, hydrogenolysis, etc.) to cut off the optically active reagent moiety, whereby the desired optical isomer is obtained. Said "optically active reagent" includes, for example, an optically active organic acids such as MTPA [α-methoxy-α-(trifluoromethyl)phenylacetic acid] and (−)-menthoxyacetic acid; and an optically active alkoxymethyl halides such as (1R-endo)-2-(chloromethoxy)-1,3,3-trimethylbicyclo[2.2.1]heptane, etc.

2-[[[3-methyl-4-(2,2,2-trifluoroethoxy)-2-pyridinyl]methyl]sulfinyl]-1H-benzimidazole or a salt thereof is produced by the methods described in JP-A-61-50978, U.S. Pat. No. 4,628,098 etc. or analogous methods thereto.

Methods of crystallization includes per se known methods, for example, a crystallization from solution, a crystallization from vapor, and a crystallization from molten form.

Methods of the "crystallization from solution" include, for example, a concentration method, a slow cooling method, a reaction method (diffusion method, electrolysis method), a hydrothermal growth method, a fusing agent method, and so forth. Solvents to be used include, for example, aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethylsulfoxide, etc.), acid amides (e.g., N,N-dimethylformamide, etc.), esters (e.g., ethyl acetate, etc.), alcohols (e.g., methanol, ethanol, isopropyl alcohol, etc.), water, and so forth. These solvents may be used singly or in mixture of two or more kinds in appropriate ratios (e.g., 1:1 to 1:100).

Methods of the "crystallization from vapor" include, for example, a gasification method (sealed tube method, gas stream method), a gas phase reaction method, a chemical transportation method, and so forth.

Methods of the "crystallization from molten form" include, for example, a normal freezing method (pulling-up method, temperature gradient method, Bridgman method), a zone melting method (zone leveling method, float zone method), a special growth method (VLS method, liquid phase epitaxis method), and so forth.

For analyzing the crystal obtained, X-ray diffraction crystallographic analysis is commonly used. In addition, crystal orientation can also be determined by a mechanical method, an optical method, etc.

Thus obtained crystal of (R)-2-[[[3-methyl-4-(2,2,2-trifluoroethoxy)-2-pyridinyl]methyl]sulfinyl]-1H-benzimidazole or a salt thereof (hereinafter also referred to as "crystal of the present invention") is useful as a pharmaceutical because it shows excellent antiulcer action, gastric acid secretion-inhibiting action, mucosa-protecting action, anti-*Helicobacter pylori* action, etc., and because it is of low toxicity. Furthermore, by crystallizing the (R)-isomer, not only its stability is improved but also its handling is facilitated so that it can be prepared as a solid pharmaceutical composition with good reproducibility. In addition, when orally administered, the crystal of the present invention is more absorbable and more rapidly shows its action than the racemate. In addition, when administered, the crystal of the present invention shows a higher Cmax (maximum blood concentration) and a greater AUC (area under the concentration-time curve) than the racemate, and becomes more unlikely to be metabolized partly because of the increased protein-binding rate, thus showing an extended duration of action. The crystal of the present invention is therefore useful as a pharmaceutical of low doses and low prevalence of adverse reactions.

The crystal of the present invention is useful in mammals (e.g., humans, monkeys, sheep, bovines, horses, dogs, cats, rabbits, rats, mice, etc.) for the treatment and prevention of digestive ulcer (e.g., gastric ulcer, duodenal ulcer, stomal ulcer, Zollinger-Ellison syndrome, etc.), gastritis, reflux esophagitis, NUD (non-ulcer dyspepsia), gastric cancer and gastric MALT lymphoma; *Helicobacter pylori* eradication; suppression of upper gastrointestinal hemorrhage due to digestive ulcer, acute stress ulcer and hemorrhagic gastritis; suppression of upper gastrointestinal hemorrhage due to invasive stress (stress from major surgery necessitating intensive management after surgery, and from cerebral vascular disorder, head trauma, multiple organ failure and extensive burn necessitating intensive treatment); treatment and prevention of ulcer caused by a nonsteroidal anti-inflammatory agent; treatment and prevention of hyperacidity and ulcer due to postoperative stress; pre-anesthetic administration etc.

The crystal of the present invention is of low toxicity and can be safely administered orally or non-orally (e.g., topical, rectal and intravenous administration, etc.), as such or in the form of pharmaceutical compositions formulated with a pharmacologically acceptable carrier, e.g., tablets (including sugar-coated tablets and film-coated tablets), powders, granules, capsules (including soft capsules), orally disintegrating tablets, liquids, injectable preparations, suppositories, sustained-release preparations and patches, in accordance with a commonly known method.

The content of the crystal of the present invention in the pharmaceutical composition of the present invention is about 0.01 to 100% by weight relative to the entire composition. Varying depending on subject of administration, route of administration, target disease etc., its dose is normally about 0.5 to 1,500 mg/day, preferably about 5 to 150 mg/day, based on the active ingredient, for example, when it is orally administered as an antiulcer agent to an adult human (60 kg). The crystal of the present invention may be administered once daily or in 2 to 3 divided portions per day.

Pharmacologically acceptable carriers that may be used to produce the pharmaceutical composition of the present invention include various organic or inorganic carrier substances in common use as pharmaceutical materials, including excipients, lubricants, binders, disintegrants, water-soluble polymers and basic inorganic salts for solid preparations; and solvents, dissolution aids, suspending agents, isotonizing agents, buffers and soothing agents for liquid preparations. Other ordinary pharmaceutical additives such as preservatives, antioxidants, coloring agents, sweetening agents, souring agents, bubbling agents and flavorings may also be used as necessary.

Such "excipients" include, for example, lactose, sucrose, D-mannitol, starch, cornstarch, crystalline cellulose, light silicic anhydride and titanium oxide.

Such "lubricants" include, for example, magnesium stearate, sucrose fatty acid esters, polyethylene glycol, talc and stearic acid.

Such "binders" include, for example, hydroxypropyl cellulose, hydroxypropylmethyl cellulose, crystalline cellulose, α-starch, polyvinylpyrrolidone, gum arabic powder, gelatin, pullulan and low-substitutional hydroxypropyl cellulose.

Such "disintegrants" include (1) crosslinked povidone, (2) what is called super-disintegrants such as crosslinked carmellose sodium (FMC-Asahi Chemical) and carmellose calcium (Gotoku Yakuhin), (3) carboxymethyl starch sodium (e.g., product of Matsutani Chemical), (4) low-substituted hydroxypropyl cellulose (e.g., product of Shin-Etsu Chemical), (5) cornstarch, and so forth. Said "crosslinked povidone" may be any crosslinked polymer having the chemical name 1-ethenyl-2-pyrrolidinone homopolymer, including polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP) and Polyplasdon INF-10 (produced by ISP).

Such "water-soluble polymers" include, for example, ethanol-soluble water-soluble polymers [e.g., cellulose derivatives such as hydroxypropyl cellulose (hereinafter also referred to as HPC), polyvinylpyrrolidone] and ethanol-insoluble water-soluble polymers [e.g., cellulose derivatives such as hydroxypropylmethyl cellulose (hereinafter also referred to as HPMC), methyl cellulose and carboxymethyl cellulose sodium, sodium polyacrylate, polyvinyl alcohol, sodium alginate, guar gum].

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogen carbonate, disodium hydrogenphosphate, etc. Such basic inorganic salts of potassium include, for example, potassium carbonate, potassium hydrogen carbonate, etc. Such basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthetic hydrotalcite [$Mg_6Al_2(OH)_{16}.CO_3.4H_2O$], alumina hydroxide magnesium, and so forth. Among others, preferred is heavy magnesium carbonate, magnesium carbonate, magnesium oxide, magnesium hydroxide, etc. Such basic inorganic salts of calcium include, for example, precipitated calcium carbonate, calcium hydroxide, etc.

Such "solvents" include, for example, water for injection, alcohol, propylene glycol, macrogol, sesame oil, corn oil and olive oil.

Such "dissolution aids" include, for example, polyethylene glycol, propylene glycol, D-mannitol, benzyl benzoate, ethanol, trisaminomethane, cholesterol, triethanolamine, sodium carbonate and sodium citrate.

Such "suspending agents" include, for example, surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose.

Such "isotonizing agents" include, for example, glucose, D-sorbitol, sodium chloride, glycerol and D-mannitol.

Such "buffers" include, for example, buffer solutions of phosphates, acetates, carbonates, citrates etc.

Such "soothing agents" include, for example, benzyl alcohol.

Such "preservatives" include, for example, p-oxybenzoic acid esters, chlorobutanol, benzyl alcohol, phenethyl alcohol, dehydroacetic acid and sorbic acid.

Such "antioxidants" include, for example, sulfites, ascorbic acid and α-tocopherol.

Such "coloring agents" include, for example, food colors such as Food Color Yellow No. 5, Food Color Red No. 2 and Food Color Blue No. 2; and food lake colors and red oxide.

Such "sweetening agents" include, for example, saccharin sodium, dipotassium glycyrrhetinate, aspartame, stevia and thaumatin.

Such "souring agents" include, for example, citric acid (citric anhydride), tartaric acid and malic acid.

Such "bubbling agents" include, for example, sodium bicarbonate.

Such "flavorings" may be synthetic substances or naturally occurring substances, and include, for example, lemon, lime, orange, menthol and strawberry.

The crystal of the present invention may be prepared as a preparation for oral administration in accordance with a commonly known method, by, for example, compression-shaping it in the presence of an excipient, a disintegrant, a binder, a lubricant, or the like, and subsequently coating it as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the crystal of the present invention as an orally disintegrating tablet, available methods include, for example, a method in which a core containing crystalline cellulose and lactose is coated with the crystal of the present invention and a basic inorganic salt, and is further coated with a coating layer containing a water-soluble polymer, to give a composition, which is coated with an enteric coating layer containing polyethylene glycol, further coated with an enteric coating layer containing triethyl citrate, still further coated with an enteric coating layer containing polyethylene glycol, and still yet further coated with mannitol, to give fine granules, which are mixed with additives and shaped. The above-mentioned "enteric coating layer" includes, for example, aqueous enteric polymer substrates such as cellulose acetate phthalate (CAP), hydroxypropylmethyl cellulose phthalate, hydroxymethyl cellulose acetate succinate, methacrylic acid copolymers [e.g., Eudragit L30D-55 (trade name; produced by Rohm), Colicoat MAE30DP (trade name; produced by BASF), Polykid PA30 (trade name; produced by San-yo Chemical)], carboxymethylethyl cellulose and shellac; sustained-release substrates such as methacrylic acid polymers [e.g., Eudragit NE30D (trade name), Eudragit RL30D (trade name), Eudragit RS30D (trade name), etc.]; water-soluble polymers; plasticizers such as triethyl citrate, polyethylene glycol, acetylated monoglycerides, triacetine and castor oil; and mixtures thereof. The above-mentioned "additive" includes, for example, water-soluble sugar alcohols (e.g., sorbitol, mannitol, multitol, reduced starch saccharides, xylitol, reduced paratinose, erythritol, etc.), crystalline cellulose [e.g., Ceolas KG 801, Avicel PH 101, Avicel PH 102, Avicel PH 301, Avicel PH 302, Avicel RC-591 (crystalline cellulose carmellose sodium)], low-substituted hydroxypropyl cellulose [e.g., LH-22, LH-32, LH-23, LH-33 (Shin-Etsu Chemical) and mixtures thereof]; binders, souring agents, bubbling agents, sweetening agents, flavorings, lubricants, coloring agents, stabilizers, excipients, disintegrants etc. are also used.

The crystal of the present invention may be used in combination with 1 to 3 other active ingredients.

Such "other active ingredients" include, for example, anti-*Helicobacter pylori* activity substances, imidazole compounds, bismuth salts, quinolone compounds, and so forth. Of these substances, preferred are anti-*Helicobacter pylori* action substances, imidazole compounds etc. Such "anti-*Helicobacter pylori* action substances" include, for example, antibiotic penicillins (e.g., amoxicillin, benzylpenicillin, piperacillin, mecillinam, etc.), antibiotic cefems (e.g., cefixime, cefaclor, etc.), antibiotic macrolides (e.g., erythromycin, clarithromycin. etc.), antibiotic tetracyclines (e.g., tetracycline, minocycline, streptomycin, etc.), antibiotic aminoglycosides (e.g., gentamicin, amikacin, etc.), imipenem. and so forth. Of these substances, preferred are antibiotic penicillins, antibiotic macrolides etc. Such "imidazole compounds" include, for example, metronidazole, miconazole, etc. Such "bismuth salts" include, for example, bismuth acetate, bismuth citrate, etc. Such "quinolone compounds" include, for example, ofloxacin, ciploxacin, etc.

Such "other active ingredients" and the crystal of the present invention may also be used in combination as a mixture prepared as a single pharmaceutical composition [e.g., tablets, powders, granules, capsules (including soft capsules), liquids, injectable preparations, suppositories, sustained-release preparations, etc.], in accordance with a commonly known method, and may also be prepared as separate preparations and administered to the same subject simultaneously or at a time interval.

BEST MODE FOR CARRYING OUT THE INVENTION

The present invention is hereinafter described in more detail by means of, but is not limited to, the following reference examples, examples and experimental examples.

In the following reference examples and examples, the term "room temperature" indicates about 15 to 30° C.

Melting points were measured using the Micro Melting Point Apparatus (produced by Yanagimoto Seisakusho), and uncorrected values are shown.

$^1$H-NMR spectra were determined with $CDCl_3$ as the solvent using Varian Gemini-200; data are shown in chemical shift δ (ppm) from the internal standard tetramethylsilane.

IR was determined using SHIMADZU FTIR-8200.

UV was determined using the HITACHI U-3200 spectrophotometer.

Optical rotation $[\alpha]_D$ was determined at 20° C. using the DIP-370 digital polarimeter (produced by JASCO).

Optical purity was determined by HPLC (column: CHIRALCEL OD 4.6 mm dia.×250 mm, temperature: about 20° C., mobile phase: hexane/2-propanol=80/20 or hexane/2-propanol=85/15, flow rate: 1.0 ml/min, detection wavelength: 285 nm) using a chiral column.

Crystal X-ray diffraction data for determining the absolute structure of sulfoxide were obtained by means of a 4-circle diffractometer (RIGAKU AFC5R) using the Cu-Kx$_\alpha$ ray. After the initial phase was determined by the direct method, the fine structure was analyzed using SHELXL-93. X-ray powder diffraction was determined using the X-ray Powder Diffraction meter Rigaku RINT2500 (ultraX18) No. PX-3.

The other symbols used herein have the following definitions:
s: singlet
d: doublet
t: triplet
q: quartet
m: multiplet
bs: broad singlet
J: binding constant

EXAMPLES

Reference Example 1

Isolation of (R)-2-[[[3-methyl-4-(2,2,2-trifluoroethoxy)-2-pyridinyl]methyl]sulfinyl]-1H-benzimidazole (R(+)-lansoprazole)

2-[[[3-methyl-4-(2,2,2-trifluoroethoxy)-2-pyridinyl]methyl]sulfinyl]-1H-benzimidazole (lansoprazole) (racemate) (3.98 g) was dissolved in the following mobile phase (330 ml) and acetonitrile (37 ml) and fractionated by HPLC (column: CHIRALCEL OD 20 mm dia.×250 mm, temperature: 30° C., mobile phase: hexane/2-propanol/ethanol=255/35/10, flow-rate: 16 ml/min, detection wavelength: 285 nm, 1 shot: 20-25 mg). Fractions of optical isomers of shorter retention time were combined and concentrated; the individual lots were combined and dissolved in ethanol and filtered through a 0.45 μm filter; after hexane was added, the filtrate was again evaporated to dryness to yield R(+)-lansoprazole (1.6 g, optical purity >97.6% ee) as an amorphous substance.

The amorphous substance obtained was subjected to fractionation and isolation in the same manner as above to yield R(+)-lansoprazole (1.37 g, optical purity >99.9% ee) as an amorphous substance.

$[\alpha]_D$=+174.3° (c=0.994%, $CHCl_3$)

Reference Example 2

Isolation of (R)-2-[[[3-methyl-4-(2,2,2-trifluoroethoxy)-2-pyridinyl]methyl]sulfinyl]-1H-benzimidazole (R(+)-lansoprazole)

Lansoprazole (racemate) (34.2 g) was dissolved in 2-propanol (1,710 ml) and hexane (1,140 ml) containing triethylamine (0.2%) and fractionated by HPLC (column: CHIRALCEL OD 50 mm dia.×500 mm, temperature: room temperature, mobile phase: hexane/2-propanol=85/15, flow rate: 60 ml/min, detection wavelength: 285 nm, 1 shot: about 300 mg) to isolate the individual optical isomers. Fractions of an optical isomer of shorter retention time were combined and concentrated; the individual lots were combined and dissolved in ethanol (250 ml); after triethylamine (3 ml) was added, the solution was filtered through a 0.45 μm filter. After the filtrate was concentrated, hexane was added, and the filtrate was again evaporated to dryness to yield R(+)-lansoprazole (9.31 g, optical purity 98.3% ee) as an amorphous substance.

Reference Example 3

Production of (R)-2-[[[3-methyl-4-(2,2,2-trifluoroethoxy)-2-pyridinyl]methyl]sulfinyl]-1H-benzimidazole (R(+)-lansoprazole)

In a nitrogen atmosphere, 2-[[[3-methyl-4-(2,2,2-trifluoroethoxy)-2-pyridyl]methyl]thio]benzimidazole (20.0 g, 0.057 mol), toluene (100 ml), water (55 mg, 0.0031 mol as based on total water content) and diethyl(+)-tartrate (2.12 ml, 0.012 mol) were mixed and stirred at 50 to 55° C. for 30 minutes. After titanium (IV) isopropoxide (1.66 ml, 0.0057 mol) was added to the mixture in a nitrogen atmosphere, the mixture was stirred at 50 to 55° C. for 1 hour. After diisopropylethylamine (3.25 ml, 0.019 mol) was added to the resulting mixed liquor under cooling in a nitrogen atmosphere, cumene hydroperoxide (30.6 ml, content 82%, 0.17 mol) was added at 0 to 5° C., followed by 3.5 hours of stirring at 0 to 5° C., to cause the reaction.

Analysis of the reaction liquor by HPLC (column: CHIRALCEL OD (Daicel Chemical Industries, Ltd.), mobile phase: hexane/ethanol=90/10, flow rate: 1.0 ml/min, detection wavelength: 285 nm) detected a sulfide at 1.32% and a sulfone at 1.81% as related substances in the reaction liquor, with no other related substances detected. The enantiomer excess rate of the title compound in said reaction liquor was 96.4% ee.

Reference Example 4

Crystal of (R)-2-[[[3-methyl-4-(2,2,2-trifluoroethoxy)-2-pyridinyl]methyl]sulfinyl]-1H-benzimidazole (R(+)-lansoprazole)

(1) In a nitrogen stream, 2-[[[3-methyl-4-(2,2,2-trifluoroethoxy)-2-pyridyl]methyl]thio]benzimidazole (4.5 kg, 12.7 mol, containing 1.89 g of water), toluene (22 l), water (25 g, 1.39 mol, or 1.49 mol if based on total water content) and diethyl(+)-tartrate (0.958 l, 5.60 mol) were mixed. In a nitrogen stream, titanium (IV) isopropoxide (0.747 l, 2.53 mol) was added to this mixture at 50 to 60° C., and the mixture was stirred at the above temperature for 30 minutes. After diisopropylethylamine (0.733 l, 4.44 mol) was added to the resulting mixed liquor at room temperature in a nitrogen stream, cumene hydroperoxide (6.88 l, content 82%, 37.5 mol) was added at −5 to 5° C., followed by 1.5 hours of stirring at −5 to 5° C., to yield a reaction liquor.

Analysis of the reaction liquor by HPLC (column: Capcell Pak (Shiseido, Co. Ltd.), mobile phase: solvent mixture (acetonitrile/water/triethylamine=50/50/1); adjusted to pH 7.0 with phosphoric acid, flow rate: 1.0 ml/min, detection wavelength: 285 nm) detected a sulfide at 1.87% and a sulfone at 1.59% as related substances in the reaction liquor, with no other related substances detected.

(2) To the reaction liquor obtained in (1) above, a 30% aqueous solution of sodium thiosulfate (17 l) was added, in a nitrogen stream, to decompose the residual cumene hydroperoxide. To the organic layer obtained by liquid separation, water (4.5 l), heptane (13.5 l), t-butyl methyl ether (18 l) and heptane (27 l) were added sequentially in this order, and this mixture was stirred to cause crystallization. The resulting crystal was separated and washed with t-butyl methyl ether-toluene (t-butyl methyl ether:toluene=4:1) (4 l) to yield a wet crystal of (R)-lansoprazole having the following powder X-ray diffraction interplanar spacings (d).

The results of powder X-ray diffraction analysis of this wet crystal are shown below.

The wet crystal yielded a powder X-ray diffraction pattern with characteristic peaks appearing at powder X-ray diffraction interplanar spacings (d) of 5.85, 4.70, 4.35, 3.66 and 3.48 Angstrom.

Analysis of this crystal by HPLC (column: CHIRALCEL OD (Daicel Chemical Industries, Ltd.), mobile phase: hexane/ethanol=90/10, flow rate: 1.0 ml/min, detection wavelength: 285 nm) detected a sulfone at 0.90% as a related substance in the crystal, with no sulfide or any other related substance detected. The (R)-lansoprazole enantiomer excess rate in this crystal was 100% ee.

(3) With stirring, a suspension in acetone (20 l) of the wet crystal obtained in (2) above was added drop by drop into a mixed liquor of acetone (7 l) and water (34 l), then water (47 l) was added. The precipitated crystal was separated and washed with acetone-water (acetone:water=1:3) (4 l) and water (12 l) to yield a wet crystal of (R)-lansoprazole having the following powder X-ray diffraction interplanar spacings (d).

The results of powder X-ray diffraction analysis of this wet crystal are shown below.

The wet crystal yielded a powder X-ray diffraction pattern with characteristic peaks appearing at powder X-ray diffraction interplanar spacings (d) of 8.33, 6.63, 5.86 and 4.82 Angstrom.

Analysis of this crystal by HPLC (column: CHIRALCEL OD (Daicel Chemical Industries, Ltd.), mobile phase: hexane/ethanol=90/10, flow rate: 1.0 ml/min, detection wavelength: 285 nm) detected no sulfone, sulfide or any other related substance in the crystal. The (R)-lansoprazole enantiomer excess rate in this crystal was 100% ee.

(4) After the wet crystal obtained in (3) above was dissolved in ethyl acetate (45 l) and water (3 l), this solution was divided into liquid layers. The trace amount of insoluble matter in the organic layer was filtered off, then triethylamine (0.2 l) was added, after which the filtrate was concentrated under reduced pressure to a liquid volume of about 7 l. To this concentrate, methanol (2.3 l), about 12.5% aqueous ammonia at about 50° C. (23 l) and t-butyl methyl ether at about 50° C. (22 l) were added, and this liquid was divided into layers. To the organic layer, about 12.5% aqueous ammonia (11 l) was added, and this liquid was divided into layers (this operation was repeated once again). The water layers were combined, and ethyl acetate (22 l) was added, and then acetic acid was added drop by drop to reach a pH of about 8 under cooling. The liquid was divided into layers, and the water layer was extracted with ethyl acetate (11 l). The organic layers were combined and washed with about 20% saline (11 l). After triethylamine (0.2 l) was added, the organic layer was concentrated under reduced pressure. Acetone (5 l) was added to the concentrate, and this mixture was concentrated under reduced pressure. The concentrate was dissolved in acetone (9 l), and this solution was added drop by drop into a mixed liquor of acetone (4.5 l) and water (22.5 l), and then water (18 l) was added drop by drop to the mixed liquor obtained. The precipitated crystal was separated and washed sequentially with cold acetone-water (acetone:water=1:3) (3 l) and water (12 l) to yield a wet crystal of (R)-lansoprazole having the following powder X-ray diffraction interplanar spacings (d).

The results of powder X-ray diffraction analysis of this wet crystal are shown below.

The wet crystal yielded a powder X-ray diffraction pattern with characteristic peaks appearing at powder X-ray diffraction interplanar spacings (d) of 8.33, 6.63, 5.86 and 4.82 Angstrom.

Analysis of this crystal by HPLC (column: CHIRALCEL OD (Daicel Chemical Industries, Ltd.), mobile phase: hexane/ethanol=90/10, flow rate: 1.0 ml/min, detection wavelength: 285 nm) detected no sulfone, sulfide or any other related substance in the crystal. The (R)-lansoprazole enantiomer excess rate in this crystal was 100% ee.

(5) The wet crystal obtained in (4) above was dissolved in ethyl acetate (32 l). The water layer was separated by a liquid separation procedure, and the organic layer obtained was concentrated under reduced pressure to a liquid volume of about 14 l. To the residual liquid, ethyl acetate (36 l) and activated charcoal (270 g) were added, after stirring, the activated charcoal was removed by filtration. The filtrate was concentrated under reduced pressure to a liquid volume of about 14 l. At about 40° C., heptane (90 l) was added drop by drop to the residual liquid. After stirring at the above temperature for about 30 minutes, the resulting crystal was separated, washed with about 40° C. ethyl acetate-heptane (ethyl acetate:heptane=1:8) (6 l), and dried to yield 3.4 kg of the title compound.

The results of powder X-ray diffraction analysis of this crystal are shown below.

The crystal yielded a powder X-ray diffraction pattern with characteristic peaks appearing at powder X-ray diffraction interplanar spacings (d) of 11.68, 6.77, 5.84, 5.73, 4.43, 4.09, 3.94, 3.89, 3.69, 3.41 and 3.11 Angstrom.

Analysis of this crystal by HPLC (column: CHIRALCEL OD (Daicel Chemical Industries, Ltd.), mobile phase: hexane/ethanol=90/10, flow rate: 1.0 ml/min, detection wavelength: 285 nm) detected no sulfone, sulfide or any other related substance in the crystal. The (R)-lansoprazole enantiomer excess rate in this crystal was 100% ee.

Example 1

Crystal of (R)-2-[[[3-methyl-4-(2,2,2-trifluoroethoxy)-2-pyridinyl]methyl]sulfinyl]-1H-benzimidazole (R(+)-lansoprazole)

Amorphous R(+)-lansoprazole as obtained in Reference Example 1 (100 mg) was dissolved in acetonitrile (1 ml), which was gradually evaporated at room temperature in a nitrogen stream. After a crystal began to form, diethyl ether (1.5 ml) was added and the container was stoppered and kept standing at room temperature.

The crystal thus formed was subjected to X-ray structural analysis, and the absolute configuration of sulfoxide was found to be the R-configuration by a method using a Flack parameter. The remaining portion of the crystal was collected by filtration, twice washed with diethyl ether (1 ml), and dried under reduced pressure, to yield crystals of R(+)-lansoprazole (38 mg).

m.p.: 144.0-144.5° C. (dec.)

Elemental Analysis

Calculated: C, 52.03; H, 3.82; N, 11.38; S, 8.68; F, 15.43; O, 8.66.

Found: C, 52.08; H, 3.76; N, 11.58; S, 8.75; F, 15.42.

$^1$H-NMR: 2.25 (3H, s), 4.40 (2H, q, J=7.8 Hz), 4.68 (1H, d, J=13.8 Hz), 4.85 (1H, d, J=13.8 Hz), 6.69 (1H, d, J=6.0 Hz), 7.29-7.39 (2H, m), 7.52 (1H, m), 7.81 (1H, m), 8.37 (1H, d, J=6.0 Hz), 11.00 (1H, bs).

IR ($\nu$ cm$^{-1}$): 3081, 3042, 2984, 1586, 1478, 1441, 1306, 1267, 1163.

UVmax (CHCl$_3$): 283.7 nm $[\alpha]_D$=+199.2° (c=0.202%, CHCl$_3$)

TABLE 1

Crystal Data and Structure Refinement Parameters

| | |
|---|---|
| Molecular formula | C$_{16}$H$_{14}$N$_3$O$_2$F$_3$S |
| Molecular weight | 369.36 |
| Crystal color, habit | Colorless, tabular |
| Crystal Dimension | 0.40 × 0.30 × 0.04 (mm) |
| Crystal system | Monoclinic |
| Lattice constants | a = 8.549(1) (Å) |
| | b = 23.350(1) (Å) |
| | c = 8.720(2) (Å) |
| | β = 103.90(1) (°) |
| | V = 1,689.8(4) (Å) |
| Space group | P2$_1$ |
| Z | 4 |
| Density (calculated) | 1.452 (g/cm$^3$) |
| Effective reflection number/parameter number | 9.12 |
| R (I ≧ 2σ(I)) | 0.036 |
| Flack parameter | −0.02(2) |

Example 2

Crystal of (R)-2-[[[3-methyl-4-(2,2,2-trifluoroethoxy)-2-pyridinyl]methyl]sulfinyl]-1H-benzimidazole (R(+)-lansoprazole)

Amorphous (R)-2-[[[3-methyl-4-(2,2,2-trifluoroethoxy)-2-pyridinyl]methyl]sulfinyl]-1H-benzimidazole as obtained in Reference Example 2 (9.17 g) was dissolved in acetone (20 ml), and water (15 ml) was added with gentle heating. After the solution was kept standing at room temperature overnight, water (20 ml) was added, followed by ultrasonication. After being collected by filtration, the solid was washed with water (30 ml, 20 ml), then washed with diisopropyl ether (20 ml), and dried under reduced pressure, to yield a solid (9.10 g). The solid obtained (9.00 g) was dissolved in acetone (30 ml), and after the solution was filtered, diisopropyl ether (50 ml) was added to the filtrate. A crystal seed was placed, and the mixture was kept standing at room temperature overnight. Precipitated crystals were collected by filtration, washed 3 times with diisopropyl ether (10 ml), and dried under reduced pressure, to yield crystals (7.85 g). The crystals obtained (7.80 g) were dissolved under heating in acetone (22.5 ml) and water (30 ml), and this solution was kept standing at room temperature for 1 hour. A precipitated solid was collected by filtration, washed with acetone-water (1:4) (15 ml), and dried under reduced pressure, to yield a solid (3.88 g). The solid obtained (3.88 g) was dissolved under heating in acetone (4 ml) and diisopropyl ether (14 ml) was added. This solution was kept standing at room temperature for 30 minutes. Precipitated crystals were collected by filtration, twice washed with diisopropyl ether (6 ml), and dried under reduced pressure, to yield crystals of R(+)-lansoprazole (3.40 g, optical purity 99.8% ee).

m.p.: 147.0-148.0° C. (dec.)

Elemental Analysis

Calculated: C, 52.03; H, 3.82; N, 11.38; S, 8.68; F, 15.43; O, 8.66.

Found: C, 51.85; H, 3.92; N, 11.26; S, 8.82; F, 15.22.

$^1$H-NMR: 2.24 (3H, s), 4.38 (2H, q, J=7.8 Hz), 4.74 (1H, d, J=13.6 Hz), 4.87 (1H, d, J=13.6 Hz), 6.68 (1H, d, J=5.8 Hz), 7.26-7.36 (2H, m), 7.45 (1H, m), 7.78 (1H, m), 8.35 (1H, d, J=5.8 Hz).

IR (vcm$^{-1}$): 3083, 3034, 2975, 1586, 1478, 1441, 1306, 1267, 1163

UVmax (CHCl$_3$): 283.6 nm $[\alpha]_D$=+180.3° (c=1.004%, CHCl$_3$)

TABLE 2

X-ray Powder Diffraction Data

| 2θ (°) | Half-value width | d-value (Å) | Relative intensity (%) |
|---|---|---|---|
| 7.560 | 0.141 | 11.6841 | 100 |
| 13.060 | 0.165 | 6.7733 | 44 |
| 15.160 | 0.141 | 5.8394 | 55 |
| 15.440 | 0.141 | 5.7342 | 84 |
| 20.040 | 0.165 | 4.4271 | 23 |
| 21.720 | 0.165 | 4.0883 | 89 |
| 22.560 | 0.141 | 3.9380 | 24 |
| 22.820 | 0.141 | 3.8937 | 24 |
| 24.080 | 0.165 | 3.6927 | 37 |
| 26.120 | 0.118 | 3.4088 | 32 |
| 28.680 | 0.165 | 3.1100 | 20 |

Example 3

Crystal of (R)-2-[[[3-methyl-4-(2,2,2-trifluoroethoxy)-2-pyridinyl]methyl]sulfinyl]-1H-benzimidazole (R(+)-lansoprazole) 1.5 Hydrate Amorphous (R)-2-[[[3-methyl-4-(2,2,2-trifluoroethoxy)-2-pyridinyl]methyl]sulfinyl]-1H-benzimidazole as obtained in Reference Example 1 (100 mg) was dissolved in ethanol (0.15 ml), and water (0.15 ml) was added. After a seed was placed, the solution was kept standing at room temperature for 1 hour. Precipitated crystals were collected by filtration, twice washed with water (2 ml), and dried under reduced pressure, to yield crystals of (R)-2-[[[3-methyl-4-(2,2,2-trifluoroethoxy)-2-pyridinyl]methyl]sulfinyl]-1H-benzimidazole (R(+)-lansoprazole) 1.5 hydrate (96 mg).

m.p.: 76.0-80.0° C.

Elemental Analysis

Calculated: C, 48.48; H, 4.32; N, 10.60; S, 8.09; F, 14.38; O, 14.13.

Found: C, 48.52; H, 4.44; N, 10.49.

TABLE 3

X-ray Powder Diffraction Data

| 2θ (°) | Half-value width | d-value (Å) | Relative intensity (%) |
|---|---|---|---|
| 6.680 | 0.165 | 13.2212 | 9 |
| 9.200 | 0.165 | 9.6046 | 21 |
| 9.960 | 0.141 | 8.8734 | 25 |
| 10.980 | 0.165 | 8.0513 | 42 |
| 13.380 | 0.141 | 6.6120 | 22 |
| 14.960 | 0.141 | 5.9170 | 63 |
| 15.680 | 0.165 | 5.6469 | 100 |
| 17.640 | 0.212 | 5.0237 | 34 |
| 19.760 | 0.212 | 4.4892 | 33 |
| 25.420 | 0.188 | 3.5010 | 23 |
| 29.800 | 0.188 | 2.9957 | 20 |

Experimental Example 1

Suppressive Action on Gastric Mucosal Injury Due to Stress of Water Immersion Restraint in Rat Male SD rats (7 weeks of age, weighing 230 to 250 g) were fasted for 24 hours, after which they were stressed by being housed in restraint cages and immersed to below the xiphoid process in a standing position in a 23° C. constant-temperature water chamber. After 5 hours, the rats were removed from the cages and sacrificed using gaseous carbon dioxide, and their stomachs excised. After the lower portion of the esophagus was clipped, a 1% formalin solution (10 ml) was injected into the stomach via the duodenum, which was then occluded, and the stomach was immersed in the same solution. After 10 minutes, an incision was made along the greater curvature, and the length (mm) of each mucosal injury was measured under a stereomicroscope. The overall sum of the injury lengths in each stomach was taken as the gastric mucosal injury index.

The crystals of (R)-2-[[[3-methyl-4-(2,2,2-trifluoroethoxy)-2-pyridinyl]methyl]sulfinyl]-1H-benzimidazole (R(+)-lansoprazole) as obtained in Example 2 were suspended in 0.5% methyl cellulose (pH 9.5) containing 0.05 M $NaHCO_3$ and orally administered at 30 minutes before stressing (dosing volume 2 ml/kg). Each treatment group comprised 9 animals. The control group (solvent administration group) and the drug administration group were compared by Steel's test.

The results are shown in Table 4.

TABLE 4

| Sample | Dose (mg/kg) | Gastric mucosal injury index (mm) | Suppression rate (%) |
|---|---|---|---|
| Control | — | 10.9 ± 1.9 | — |
| (R)-lansoprazole crystal | 3 | 0.2 ± 0.2* | 98.0 |

Each figure of gastric mucosal injury index is the mean ± standard error for the 9 animals in each group.
*p < 0.01 (versus control group, Steel's test)

Experimental Example 2

The crystals of R(+)-lansoprazole as obtained in Example 2 (about 5 mg) and amorphous R(+)-lansoprazole as obtained in Reference Example 1 (about 5 mg) were each taken in a colorless glass bottle, and their stability during storage at 60° C. (stopper removed) was examined. A 25 ml solution (concentration: about 0.2 mg/ml) of the sample after completion of storage in the mobile phase, along with a standard solution prepared using the initial lot, was analyzed under the HPLC conditions shown below, and the R(+)-lansoprazole content (residual percentage) was calculated from the peak area obtained. The results are shown in Table 5.

| HPLC analytical conditions | |
|---|---|
| Detection wavelength | UV 275 nm |
| Column | YMC Pro C18, 4.6 × 150 mm |
| Mobile phase | Fluid prepared by adding phosphoric acid to water/acetonitrile/triethyl amine (63:37:1) to reach pH 7. |
| Flow rate | 1.0 ml/min |
| Column temperature | 40° C. |
| Sample injection volume | 10 μl |

TABLE 5

Stability of R(+)-Lansoprazole Crystal and Amorphous

| Sample | Duration of storage | Description | Content (Residual percentage) |
|---|---|---|---|
| Crystal | 1 week | Light-brown | 97.0 |
| | 2 weeks | Brown | 93.8 |
| | 4 weeks | Brown | 91.7 |
| Amorphous | 1 week | Brown | 70.8 |
| | 2 weeks | Blackish brown | 57.5 |

When the sample was stored at 60° C. (exposed), the crystal of Example 2 retained a content exceeding 90% for up to 4 weeks, whereas the amorphous form of Reference Example 1 showed reduction in content to 70.8% after 1 week and 57.5% after 2 weeks. This finding demonstrates that the crystal of R(+)-lansoprazole is more stable and more preferable for use as a pharmaceutical etc. than the amorphous form.

INDUSTRIAL APPLICABILITY

The crystal of the present invention is useful as a pharmaceutical because it shows excellent antiulcer action, gastric acid secretion-inhibit action, mucosa-protecting action, anti-*Helicobacter pylori* action etc., and because it is of low toxicity. Furthermore, by crystallizing the (R)-isomer, not only its stability is improved but also its handling is facilitated so that it can be prepared as a solid pharmaceutical composition with good reproducibility. In addition, when orally administered, the crystal of the present invention is more absorbable and more rapidly shows its action than the racemate. In addition, when administered, the crystal of the present invention shows a higher Cmax and a greater AUC than the racemate, and becomes more unlikely to be metabolized partly because of the increased protein-binding rate, thus showing an extended duration of action. The crystal of the present invention is therefore useful as a pharmaceutical of low doses and low prevalence of adverse reactions.

The invention claimed is:

1. An amorphous compound of (R)-2-[[[3-methyl-4-(2,2,2-trifluoroethoxy)-2-pyridinyl]methyl]sulfinyl]-1H-benzimidazole or a salt thereof.

2. A pharmaceutical composition comprising the amorphous compound according to claim 1 and a pharmaceutically acceptable excipient, carrier or diluent.

3. A pharmaceutical composition according to claim 2, wherein the pharmaceutical composition includes an effective amount of the amorphous compound to treat or prevent digestive ulcer.

4. A method for treating or preventing digestive ulcer, which comprises administering to a mammal in need thereof an effective amount of the amorphous compound of claim 1.

* * * * *